(12) United States Patent
Klimov et al.

(10) Patent No.: US 7,261,940 B2
(45) Date of Patent: Aug. 28, 2007

(54) MULTIFUNCTIONAL NANOCRYSTALS

(75) Inventors: Victor I. Klimov, Los Alamos, NM (US); Jennifer A. Hollingsworth, Los Alamos, NM (US); Scott A. Crooker, Los Alamos, NM (US); Hyungrak Kim, Albuquerque, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 70 days.

(21) Appl. No.: 11/004,167

(22) Filed: Dec. 3, 2004

(65) Prior Publication Data

US 2006/0118757 A1 Jun. 8, 2006

(51) Int. Cl.
*B32B 5/66* (2006.01)

(52) U.S. Cl. .................... 428/403; 428/404; 428/405; 428/406

(58) Field of Classification Search ................ 428/403, 428/404, 405, 406
See application file for complete search history.

(56) References Cited

U.S. PATENT DOCUMENTS

| | | |
|---|---|---|
| 6,322,901 B1 | 11/2001 | Bawendi |
| 6,878,871 B2 * | 4/2005 | Scher et al. ................ 136/252 |
| 2004/0105980 A1 | 6/2004 | Sudarshan et al. |

OTHER PUBLICATIONS

Gu et al., "Facile One-Pot Synthesis of Bifuncitonal Heterodimers of Nanoparticles: A Conjugate of Quantum Dot and Magnetic Nanoparticles," J. Am. Chem. Soc. 2004, 126, 5664-65.
Kim et al., "Synthesis and characterization of Co/CdSe core/shell nanocomposites: Bifunctional magnetic-optical nanocrystals," J. Am. Chem. Soc. 2005, 127, 544-46.
Lu et al., "Modifying the Surface Properties of Superparamagnetic Iron Oxide Nanoparticles Through A Sol-Gel Approach," Nano Lett., vol. 2, No. 3, 183-186, 2002.
Redl et al., "Three-dimensional Binary Superlatticese of Magnetic Nanocrystals and Semiconductor Quantum Dots," Nature, vol. 423, 968-971, Jun. 2003.
Sobal, et al. "Synthesis of Core-Shell PtCo Nanocrystals," J. Phys. Chem. B 2003, 107, 7351-54.
Talaphin et al., "CdSe and CdSe/CdS Nanorod Solids," J. Am. Chem. Soc. 2004, 126, 12984-88.

* cited by examiner

*Primary Examiner*—Leszek Kiliman
(74) *Attorney, Agent, or Firm*—Bruce H. Cottrell; Holly L. Teeter

(57) ABSTRACT

Multifunctional nanocomposites are provided including a core of either a magnetic material or an inorganic semiconductor, and, a shell of either a magnetic material or an inorganic semiconductor, wherein the core and the shell are of differing materials, such multifunctional nanocomposites having multifunctional properties including magnetic properties from the magnetic material and optical properties from the inorganic semiconductor material. Various applications of such multifunctional nanocomposites are also provided.

19 Claims, 5 Drawing Sheets

FIGURE 2A
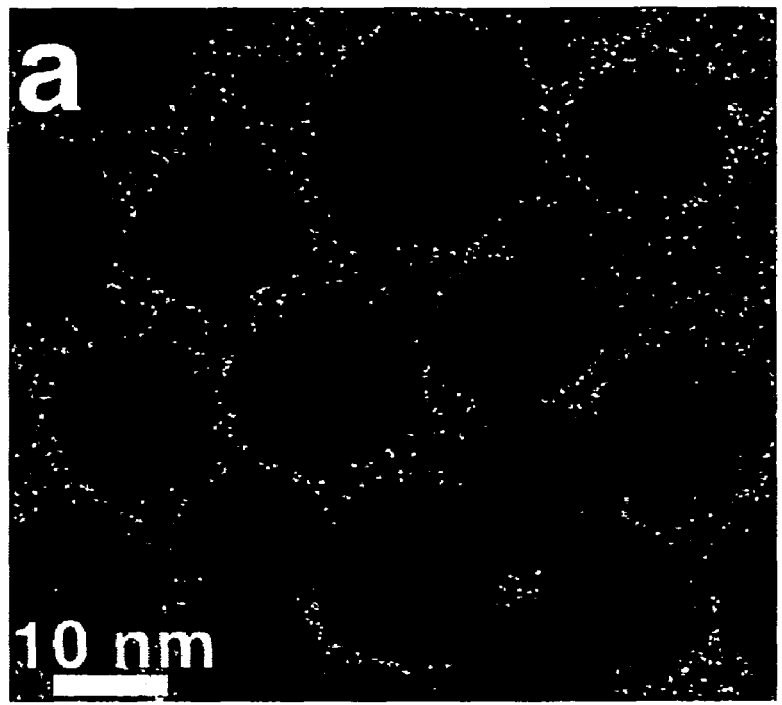
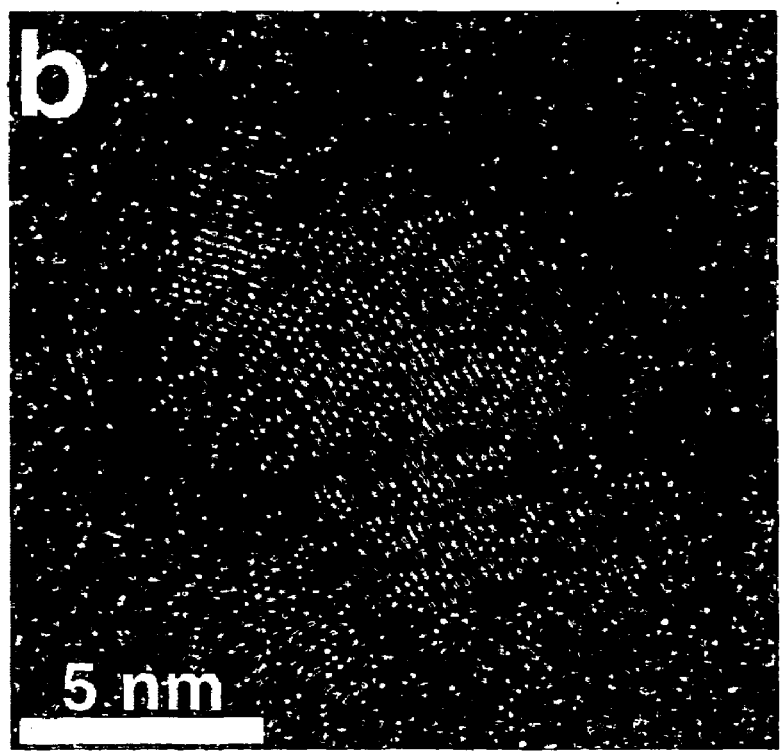
FIGURE 2B

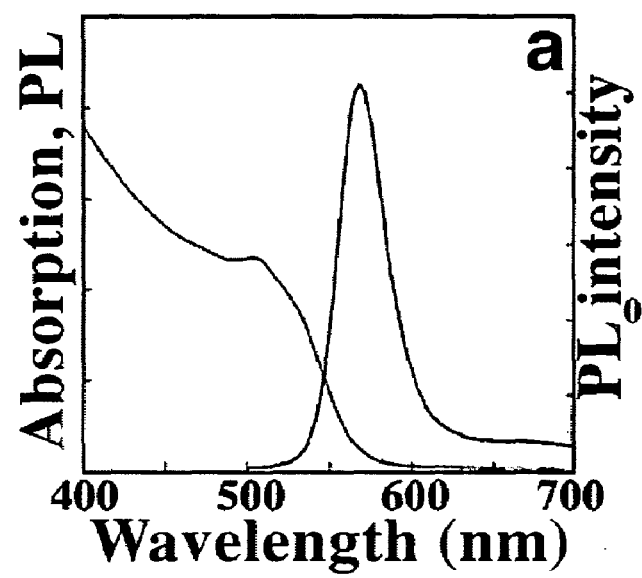 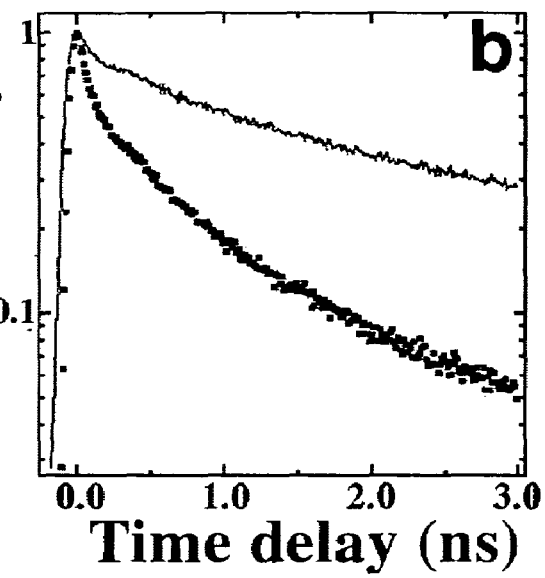
FIGURE 5A            FIGURE 5B

MULTIFUNCTIONAL NANOCRYSTALS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to all-inorganic multifunctional nanocrystals, e.g., bifunctional nanocrystals, especially all-inorganic bifunctional nanocrystals.

BACKGROUND OF THE INVENTION

Nanocomposite materials provide the possibility for enhanced functionality and multi-functional properties in contrast with more-limited single-component counterparts. One example of a nanocomposite material is the inorganic core-shell structure. In the case where semiconductors comprise the core and shell, the core-shell motif has permitted enhanced photoluminescence, improved stability against photochemical oxidation, enhanced processibility, and engineered band structures. Where metals have been combined in core-shell structures, noble metals have been grown on magnetic metal cores and the reverse, for example, causing changes in magnetic, optical and chemical properties compared to the properties of the individual components. While examples of enhancement or modification of properties resulting from the core-shell structures are becoming more common, instances of truly multifunctional behavior remain rare. For example, iron oxide nanoparticles overcoated with a dye-impregnated silica shell were shown to retain the magnetic properties of the core, while exhibiting the luminescent optical properties of the organic dye.

SUMMARY OF THE INVENTION

In accordance with the purposes of the present invention, as embodied and broadly described herein, the present invention provides a composite nanoparticle having multifunctional properties comprising a core of a material such as a magnetic material or an inorganic semiconductor; and, a shell of a material such as a magnetic material or an inorganic semiconductor, the core and shell of differing materials and such multifunctional properties including magnetic properties from the magnetic material and optical properties from the inorganic semiconductor material.

The present invention further provides a process of forming such composite nanoparticles.

The present invention still further addresses uses or applications of such composite nanoparticles including applications such as: an improved detection/characterization of biomolecules by taking advantage of multifunctional properties of the composite nanocrystal, e.g., an optical reporter function for detection coupled with a magnetic label for collection, where the ability to tune the blocking temperature of the magnetic component by altering nanocrystal surface properties imparts additional flexibility in applications by allowing fine temperature control over ferromagnetic-superparamagnetic phase transition that can be used to control dispersibility of composite nanocrystal-labeled biomolecules; an improved asset label/tag; an improved source of spin-polarized electrons and holes for spin injectors; and, a component for magnetic field-modulated emitters.

BRIEF DESCRIPTION OF THE DRAWINGS

FIG. 2(a) shows a digital representation of a transmission electron micrograph (TEM) image of Co/CdSe core/shell nanocomposites and FIG. 2(b) shows a digital representation of a high resolution TEM image of a composite nanocrystal revealing the polycrystalline nature of this shell.

FIG. 5(a) shows UV absorption and photoluminescence (PL) spectra of Co/CdSe core/shell nanocomposites and FIG. 5(b) shows normalized PL dynamics taken at 20 K of CdSe nanocrystals (grey line) and Co/CdSe core/shell nanocrystals (dotted line), after subtracting the contribution of the slow PL dynamics of the CdSe nanocrystals that are synthesized simultaneously at a small fraction (observed as a minor sample component in TEM studies) with the Co/CdSe core/shell nanocrystals. The straight line is an exponential fit with a time constant of 0.7 nanoseconds (ns).

DETAILED DESCRIPTION

The present invention is concerned with multifunctional nanocomposites or multifunctional nanocrystals, e.g., bifunctional nanocrystals, especially all-inorganic bifunctional nanocrystals. In particular, the present invention is concerned with magnetic and luminescent nanocrystals. The multifunctional nanocomposites or multifunctional nanocrystals of the present invention can be especially useful as labels or tags in biological applications and the like due to the combination of, e.g., magnetic properties and optical properties.

Figure 1A:
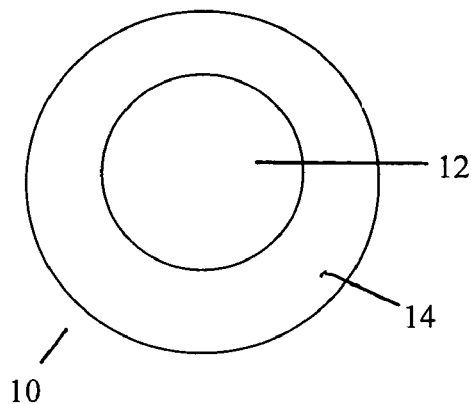
FIG. 1(a) shows a first embodiment of a core/shell nanocomposite in accordance with the present invention.
Figure 1B:
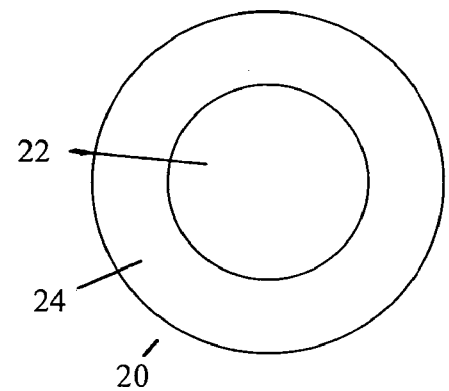
FIG. 1(b) shows a second embodiment of a core/shell nanocomposite in accordance with the present invention.

The present invention provides an all-inorganic multifunctional nanocomposite. In one embodiment as shown in FIG. 1(a), such a multifunctional nanocomposite 10 includes a magnetic material core 12 such as Co, and an inorganic semiconductor shell 14 such as CdSe. This type of structure, i.e., a Co core and a CdSe shell, is an example of an all-inorganic bi-functional nanoparticle, such a core/shell combination possessing both magnetic and luminescent properties within a single all-inorganic quantum dot. In another embodiment as shown in FIG. 1(b), such a multifunctional nanocomposite 20 includes an inorganic semiconductor core 22 such as CdSe, and a magnetic material shell 24 such as Co. This type of structure, i.e., a CdSe core and a Co shell, is another example of an all-inorganic bi-functional nanoparticle possessing both magnetic and luminescent properties within a single all-inorganic quantum dot. The present invention further provides a new, efficient source of spin-polarized electrons and holes for spintronics applications. The present invention still further provides field-modulated nanocrystal emitters.

The nanocomposites are generally members of a crystalline population having a narrow size distribution (standard deviation ≦20%), although the size distribution can be broadened if desired. The shape of the nanocomposites can be a sphere, a rod, a wire, a disk, a branched structure and the like.

In one embodiment of the present invention, the nanocomposite includes a magnetic material core and an inorganic semiconductor shell, while in another embodiment, the nanocomposite includes an inorganic semiconductor core and a magnetic material shell. The magnetic material cores or magnetic material shells can generally be of metals such as cobalt, nickel, iron, iron-platinum (FePt), an iron oxide such as, e.g., $Fe_2O_3$ or $Fe_3O_4$, and a magnesium iron oxide spinel such as $MgFe_2O_4$ and the like.

The shells in the present invention are generally uniform about the entirety of the core, i.e., a wholly complete shell is desired about the core. Typically, cores will have at least one dimension between about 1.5 nm and 30 nm. This complete shell is desired whether the core is a metallic material core or an inorganic semiconductor core. The shells can be formed upon the core as either single crystalline materials or as polycrystalline materials depending upon deposition conditions and lattice matching between the underlying material and the shell material. Generally, the shells of an active material will be from about 0.3 nm to about 3 nm in thickness.

The optically active semiconductor cores or shells can be of an inorganic material selected from among Group II-VI compounds, Group II-V compounds, Group III-VI compounds, Group III-V compounds, Group IV-VI compounds, Group I-III-VI compounds, Group II-IV-V compounds, and Group II-IV-VI compounds. By "optically active" is meant that these materials can absorb or emit light such optical properties dependent upon composition, location or size (dimension). Examples include cadmium sulfide (CdS), cadmium selenide (CdSe), cadmium telluride (CdTe), zinc sulfide (ZnS), zinc selenide (ZnSe), zinc telluride (ZnTe), mercury sulfide (HgS), mercury selenide (HgSe), mercury telluride (HgTe), aluminum nitride (AlN), aluminum phosphide (AlP), aluminum arsenide (AlAs), aluminum antimonide (AlSb), gallium arsenide (GaAs), gallium nitride (GaN), gallium phosphide (GaP), gallium antimonide (GaSb), indium arsenide (InAs), indium nitride (InN), indium phosphide (InP), indium antimonide (InSb), thallium arsenide (TlAs), thallium nitride (TlN), thallium phosphide (TlP), thallium antimonide (TlSb), lead sulfide (PbS), lead selenide (PbSe), lead telluride (PbTe), zinc cadmium selenide (ZnCdSe), indium gallium nitride (InGaN), indium gallium arsenide (InGaAs), indium gallium phosphide (InGaP), aluminum indium nitride (AlInN), indium aluminum phosphide (InAlP), indium aluminum arsenide (InAlAs), aluminum gallium arsenide (AlGaAs), aluminum gallium phosphide (AlGaP), aluminum indium gallium arsenide (AlInGaAs), aluminum indium gallium nitride (AlInGaN) and the like, mixtures of such materials, or any other semiconductor or similar materials. The inorganic semiconductor shell upon the magnetic material core can include a single optically active inorganic semiconductor shell or can include multiple optically active inorganic semiconductor shells for selective tuning of the properties. Such multiple inorganic semiconductor shells can be of differing inorganic semiconductor materials. For example, a composite nanocrystal could include a cobalt core, an active shell layer of CdSe and a second active shell layer of CdTe.

Additionally, it can be important to surface passivate the multifunctional nanocomposites by overcoating the nanocomposites with a shell of a wide-gap semiconductor, e.g., zinc sulfide. Thus, where there is a shell of an inorganic semiconductor material upon a magnetic material core, the inorganic semiconductor shell can have an overcoating on the outer surface of the shell. Such an overcoating can also be a semiconductor material, such an overcoating having a composition different than the composition of the core, but generally having a band gap that is larger than the band gap of the underlying inorganic semiconductor shell material. The overcoat on the surface of the multifunctional nanocomposites can include materials selected from among Group II-VI compounds, Group II-V compounds, Group III-VI compounds, Group III-V compounds, Group IV-VI compounds, Group I-III-VI compounds, Group II-VI-VI compounds, and Group II-IV-V compounds. Examples include cadmium sulfide (CdS), cadmium telluride (CdTe), zinc sulfide (ZnS), zinc selenide (ZnSe), zinc telluride (ZnTe), mercury sulfide (HgS), mercury selenide (HgSe), mercury telluride (HgTe), aluminum nitride (AlN), aluminum phosphide (AlP), aluminum arsenide (AlAs), aluminum antimonide (AlSb), gallium arsenide (GaAs), gallium nitride (GaN), gallium phosphide (GaP), gallium antimonide (GaSb), indium arsenide (InAs), indium nitride (InN), indium phosphide (InP), indium antimonide (InSb), thalium arsenide (TlAs), thallium nitride (TlN), thallium phosphide (TlP), thallium antimonide (TlSb), lead sulfide (PbS), lead selenide (PbSe), lead telluride (PbTe), mixtures of all such materials, or any other semiconductor or similar materials.

Suitable overcoatings can generally be applied as described in U.S. Pat. No. 6,322,901 by Bawendi et al. wherein overcoatings were applied to nanocrystalline quantum dots, such description incorporated herein by reference.

Figure 1C:
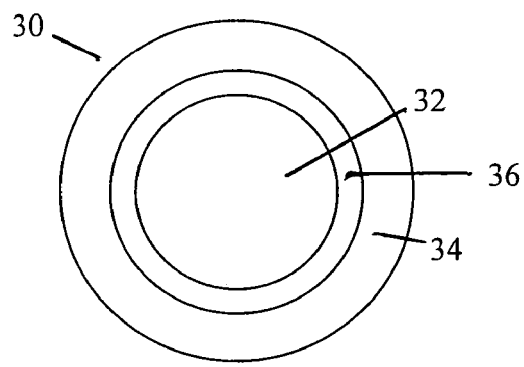
FIG. 1(c) shows an embodiment of a core/shell nanocomposite with a spacer layer in accordance with the present invention; and, FIG. 1(d) shows another embodiment of a core/shell nanocomposite with a spacer layer in accordance with the present invention.
Figure 1D:
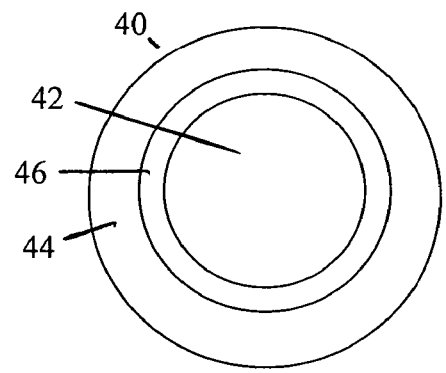

In one embodiment of the present invention as shown in FIG. 1(c), a spacer layer 36 is employed between a magnetic material core 32 and an inorganic semiconductor shell 34 of a multifunctional nanocomposite 30 in order to minimize potential quenching of the shell properties by the magnetic material core. In another embodiment as shown in FIG. 1(d), a spacer layer 46 is employed between an inorganic semiconductor core 42 and magnetic material shell 44 of multifunctional nanocomposite 40 in order to minimize potential quenching of the core semiconductor properties by the magnetic material shell. Such spacers can typically be of (a) inorganic semiconductors that are essentially functioning solely as a spacer material without any contribution of electronic properties from that material to the overall structure or (b) dielectric materials such as silica and the like. The "non-active" spacer layer may also function to minimize lattice strain between "active" layers.

The multifunctional nanocomposites of the present invention offer unique possibilities for bioassay labeling or tagging applications where optical properties (e.g., emission) of the shell facilitate optical detection of tagged biomolecules or physical assets, respectively, and the magnetic properties of the core facilitate magnetic collection of tagged biomolecules or adherence of tags to certain physical assets, respectively. Further, the ability to tune certain properties such as blocking temperature (the transition from superparamagnetic to ferromagnetic behavior), would allow, e.g., reversible sample aggregation. That is, for sample temperatures below the blocking temperature, the tag would be ferromagnetic, facilitating agglomeration under an applied magnet. Raising the sample temperature above the blocking temperature would cause a transition to the superparamagnetic state and facilitate re-dissolution/separation of the tagged biomolecules, facilitating further characterization of the sample.

The multifunctional nanocomposites of the present invention may also offer a unique efficient source of spin-polarized electrons and holes for "semiconductor spintronics" applications, making them truly multifunctional. Present day spin injectors, based on passing current from a ferromagnetic contact into a semiconductor, are limited to less than about 10 percent efficiency due largely to conductivity mismatch at the interface. Due to the uniquely intimate contact between a magnetic and semiconducting material provided by the nano core/shell or nano segmented structures, such hybrid nanocomposites may circumvent the problems of current spin injectors.

The multifunctional nanocomposites of the present invention may also provide magnetic-field-modulated emitters, where the photoluminescence from the semiconductor component is field tunable due to the influence of the magnetic component on the semiconductor spin structure.

The present invention also provides a process of forming composite nanoparticles, each composite nanoparticle including a core of either a magnetic material or an inorganic semiconductor material and a shell of either a magnetic material or an inorganic semiconductor material, the core and shell being of differing materials. The process involves suspending or solvating nanoparticles of either a magnetic material or an inorganic semiconductor material within a liquid medium (such nanoparticles being the core), introducing precursors for a shell of either a magnetic material or an inorganic semiconductor material into the liquid medium; and, reacting the precursors under conditions capable of obtaining deposition wherein the shell is formed on the core nanoparticles. In the instance of Co nanoparticles as the core and cadmium selenide as the shell material, the conditions capable of achieving deposition wherein the CdSe shell is formed on the Co core nanoparticles can be at reaction temperatures of from about 70° C. to about 200° C., more preferably from about 120° C. to about 200° C. For other systems, such optimal temperature ranges will likely vary between about 70° C. to about 300° C. as can be readily determined by one skilled in the art. Other conditions than temperature such as precursor concentration, core material concentration, concentration of other ligands and addition methods of the materials may be determinative of the desired deposition as well.

A synthetic method has been developed for the preparation of truly bi-functional, all inorganic NCs that combine the properties of magnetic nanoparticles and semiconductor quantum dots for the first time in a core/shell arrangement. While the nanocomposites retain the optical and magnetic properties of the component parts, permitting potential applications that would make use of this novel bifunctionality, e.g., optical "reporters" coupled with magnetic "handles" for use in bioassays, the respective properties are altered due to the unique core/shell structure.

The present invention is more particularly described in the following examples that are intended as illustrative only, since numerous modifications and variations will be apparent to those skilled in the art.

EXAMPLE 1

Co/CdSe core/shell nanocomposites were prepared by controlled CdSe deposition onto preformed Co nanocrystals (NCs). The Co NCs were synthesized by high temperature decomposition of organometallic precursors, $Co_2(CO)_2$, in the presence of organic surfactant molecules. After the reaction, the Co NCs were precipitated by the addition of a non-solvent, anhydrous methanol, and re-dissolved in a nonpolar solvent such as toluene or hexane. By repeating this process, the Co NCs were effectively "washed" and excess surfactant was removed. For the core/shell preparation, washed Co NCs (2.7 mmole) were dispersed in n-Hexane (about 2 mL). Trioctylphosphine oxide (TOPO, 99%; 10 g) and hexadecylamine (HDA, 99%; 5 g) were then heated to 120° C. under vacuum in a reaction flask. After two hours, the TOPO and HDA were placed under nitrogen and heated to 140° C. A small portion of this mixture (about 1 mL) was added to the Co NCs, and additional hexane was added if the resulting solution was very thick. This solution was then transferred back into the reaction flask. CdSe precursors [dimethylcadmium, 1.35 mmole, and Se, 1.5 mmole dissolved in 1.5 mL trioctylphosphine (TOP), in 5 mL additional TOP] were added dropwise into the vigorously stirred mixture. The reaction was held at temperature overnight. The low reaction temperature (in comparison with a conventional CdSe synthesis) required a long incubation time. Further, higher temperatures (>200° C.) resulted in exclusively homogeneous nucleation and growth of CdSe NCs, unassociated with the Co NCs. While the lower-temperature preparation did generate some fraction of both uncoated Co cores and unassociated CdSe NCs, the various fractions were isolable using a combination of standard size-selective precipitation/washing steps followed by magnetic separations. In general, methanol was used to destabilize the solutions, resulting first in precipitation of Co cores (brown solid) that could be redissolved in dichlorobenzene. CdSe NCs and Co/CdSe core/shell NCs were both soluble in hexane but could be separated by size. Further, by placing a magnet near a methanol-destabilized suspension, the core/shell NC component attracted to the magnet. The emission from the composite particles was easily seen when excited by a hand-held fluorescent lamp.

The core Co NCs are reasonably monodisperse (±15-20%) with a diameter of about 11 nm. The Co/CdSe core/shell NCs retain the spherical shape of the seed core and exhibit a uniform shell that is 2 to 3 nm thick (FIG. 2(a) and FIG. 2(b)). The contrast between the Co-core and CdSe-shell is easily distinguishable by conventional TEM microscopy (FIG. 2(a)), with the precise nanostructure of the shell visible in high resolution (HR) imaging. As a possible mechanism for shell growth, we suggest a random, highly non-epitaxial, nucleation of CdSe on the Co surface followed by CdSe particle growth and nanocrystallite merging. The low growth temperature used for the CdSe deposition likely supports primarily heterogeneous rather than homogeneous nucleation, and the uniformity of the shell suggests a sufficient annealing process to build a complete coating.

Figure 3:
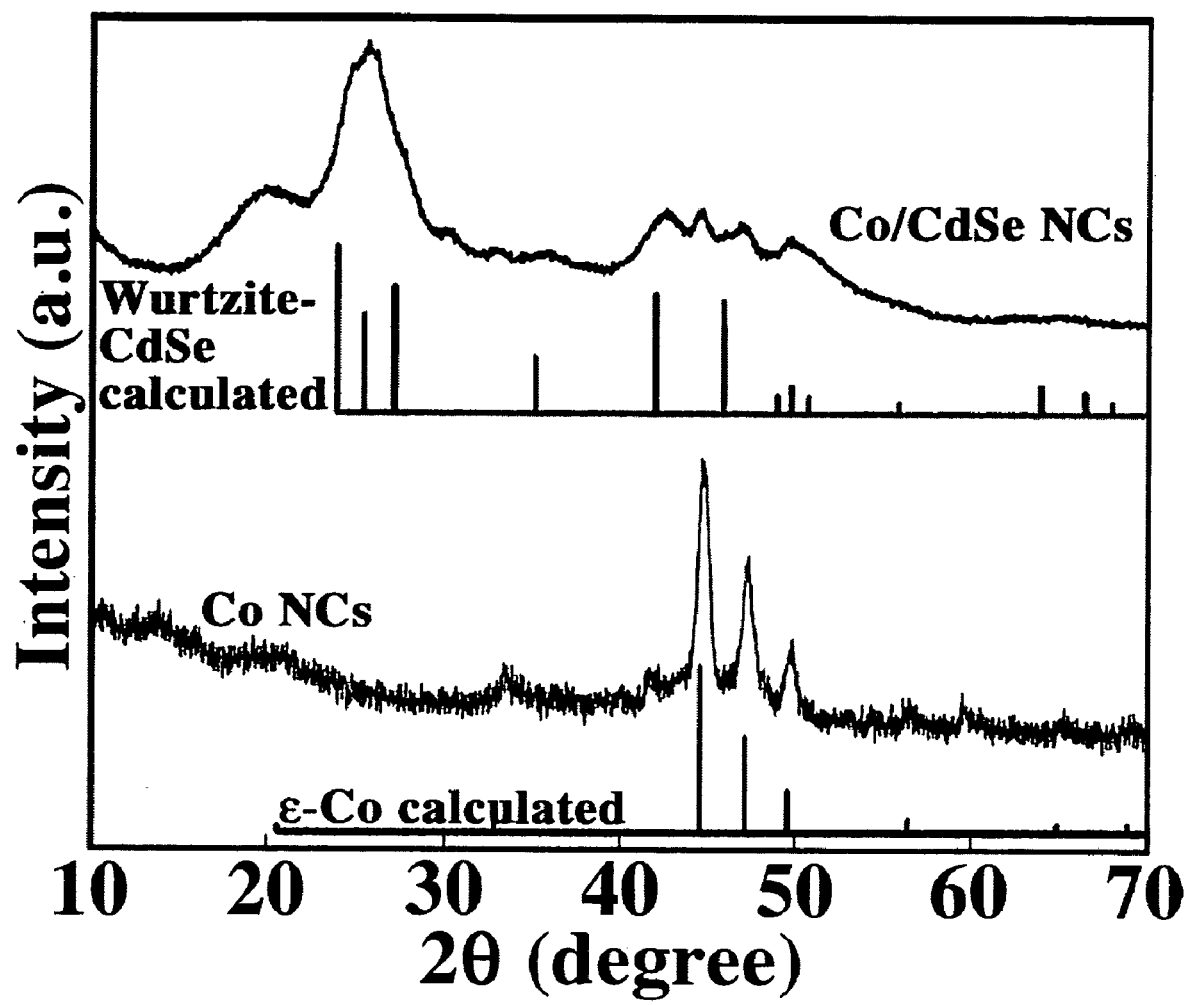
FIG. 3 shows XRD patterns for Co nanocrystals and Co/CdSe core/shell nanocrystals compared to calculated patterns for $\epsilon$-Co and wurtzite CdSe.

As determined by powder x-ray diffraction (XRD) (FIG. 3), the Co NCs grow as the ϵ-Co phase, which is typical of the preparative method employed here. The Co/CdSe core/shell NCs yield an XRD pattern that contains additional diffraction peaks which can be indexed to wurtzite-CdSe (confirmed in HR-TEM: about 2.2 Å and about 2.6 Å lattice spacings match the (11) and (102) crystal planes of wurtzite CdSe). The added broadness of the XRD reflections in the composite-structure pattern results from the very small domain size characteristic of the polycrystalline CdSe shell.

Figure 4A:
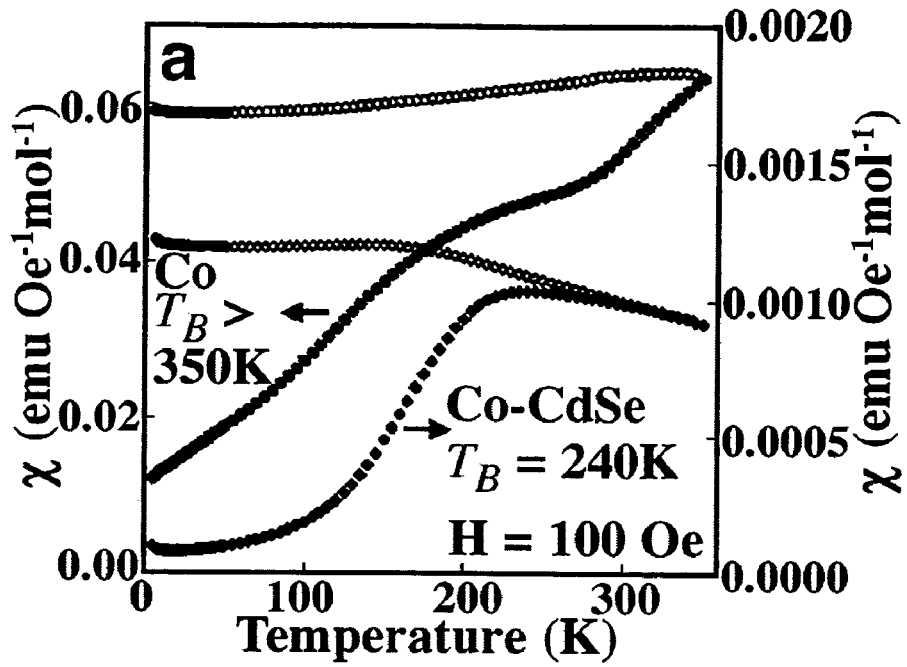
FIG. 4(a) shows temperature dependence of the magnetization for field cooled (open circles) and zero field cooled (filled circles) Co nanocrystals and Co/CdSe core/shell nanocrystals (traces intersect at the blocking temperature, the transition from superparamagnetic to ferromagnetic behavior)
Figure 4B:
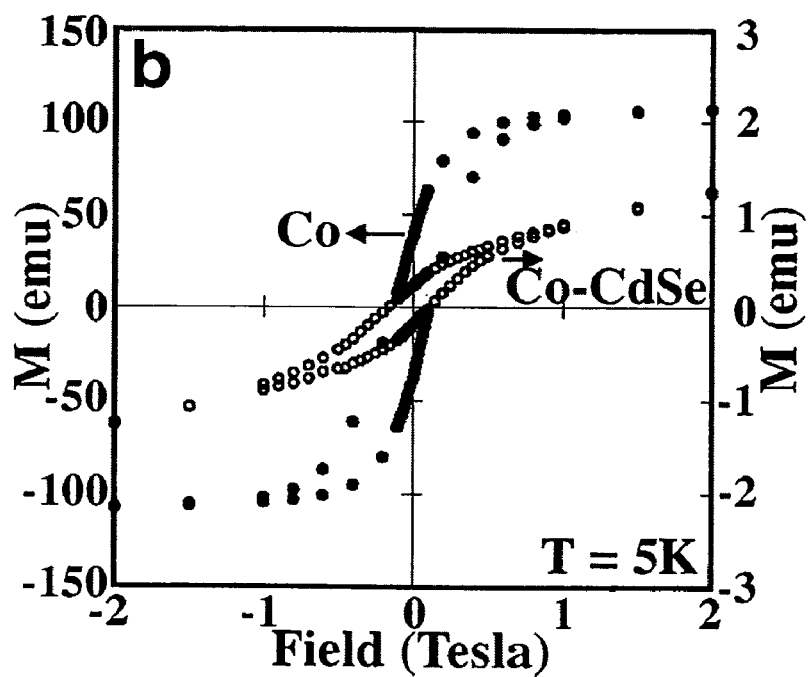
FIG. 4(b) shows the field dependence of the magnetization for the same samples.

DC magnetization as a function of temperature in an applied magnetic field of 100 Oe was recorded for the Co and the Co/CdSe NCs (FIG. 4(a)). For 11 nm ϵ-Co NCs, the blocking temperature, $T_B$, is above 350 K, but the transition from super-paramagnetic to ferromagnetic behavior after CDSE-shell coating occurs at approximately 240 K (FIG. 4(a)). Since no significant change in Co-core size and shape was observed in TEM, the decrease in blocking temperature was observed when magnetic-optical nanocrystals were prepared as dimmers. The coercivity, the strength of a demagnetizing field required to coerce a magnetic particle to change magnetization direction, $H_c$, was also determined and found to be nearly the same for both samples, 0.11 Tesla (FIG. 4(b)), although there is a large drop in saturation magnetization per gram in the core/shell structures due to the presence of the nonmagnetic CdSe phase. The coercivity of single-domain NCs depends mainly on the magnet-crystalline anisotropy and the domain size of the particles. The consistency in coercivity between the two samples correlates well with TEM observations that magnetic-core particle size did not change appreciably. Further, it indicates that the coercivity is determined mainly by magneto-crystalline anisotropy, rather than surface anisotropy which would be sensitive to surface modification.

Absorption and emission spectra of the core/shell nanocomposites are presented in FIG. 5(a). The observations of a relatively large Stokes shift further distinguishes the core-shell NCs from pure CdSe quantum dots. Monodisperse CdSe nanoparticle solutions of similarly sized NQDs exhibit a Stokes shift of about 20 nm, compared to the nanocomposites' 40-50 nm shift. While the large Stokes shift may be related to the effect of the presence of a close-proximity nanomagnet on the semiconductor optical properties, it can also be attributed to CdSe shape anisotropy. Specifically, the crystallite domains visible in high-resolution TEM (FIG. 2(b)) are approximately 2×3 nm in size. The absorption edge roughly correlates with a CdSe NC having these dimensions, but the photoluminescence (PS) maximum is shifted. Likely, pairs of neighboring domains are sufficiently well associated such that they behave as single "nanorods" causing the observed Stokes shift—similar to CdSe nanorod samples, where the Stokes shift is large compared to approximately spherical particles. For the Co/CdSe NCs we obtain a quantum yield (QY) in emission of about 2 to 3%. While not optimized, this is comparable to QYs (5 to 6%) obtained for CdSe prepared by similar preparative routes without, for example, ZnS overcoating to enhance emission efficiency. In addition, it was found that the PL dynamics of the Co/CdSe NCs are distinctly different from that for CdSe NCs (FIG. 5(b)). At low temperatures (20K), where trapping of excited carriers is strongly reduced, and therefore PL dynamics of NCs is normally dominated by relatively slow radiative decay (time constant >50 ns), we observe that the PL of the core/shell NCs decays very rapidly, within less than 1 nanosecond. These preliminary results suggest that the accelerated PL decay is the result of CdSe shell emission quenching the presence of the metallic Co core, although it may also result from a modified exciton spin structure induced by magnetic interactions.

Although the present invention has been described with reference to specific details, it is not intended that such details should be regarded as limitations upon the scope of the invention, except as and to the extent that they are included in the accompanying claims.

What is claimed is:

1. A composite nanoparticle comprising:
    a core of a material selected from the group consisting of a magnetic material and an inorganic semiconductor; and,
    a shell of a material selected from the group consisting of an inorganic semiconductor and a magnetic material, wherein said core and said shell are of differing materials and said composite nanoparticle is characterized as having multifunctional properties including magnetic properties from said magnetic material and optical properties from said inorganic semiconductor material.

2. The composite nanoparticle of claim 1 including a multiplicity of nanoparticles wherein said cores have a monodisperse size distribution.

3. The composite nanoparticle of claim 1 wherein said core includes multiple layers of at least two active inorganic semiconductors.

4. The composite nanoparticle of claim 1 wherein said shell includes multiple layers of at least two active inorganic semiconductors.

5. The composite nanoparticle of claim 1 wherein said core has at least one dimension of between about 1.5 nm and about 30 nm.

6. The composite nanoparticle of claim 1 wherein said shell is from about 0.3 nm to about 3 nm in thickness.

7. The composite nanoparticle of claim 1 wherein said shell is single crystalline or polycrystalline.

8. The composite nanoparticle of claim 1 wherein said core has a structure selected from the group consisting of spheres, rods, wires, and branched structures.

9. The composite nanoparticle of claim 1 wherein said core is of a magnetic material selected from the group consisting of cobalt, nickel, iron, iron-platinum, iron oxide, and a magnesium iron oxide spinel.

10. The composite nanoparticle of claim 1 wherein said core is of an inorganic semiconductor material selected from the group consisting of Group II-VI compounds, Group II-V compounds, Group III-VI compounds, Group III-V compounds, Group IV-VI compounds, Group I-III-VI compounds, Group II-IV-V compounds, and Group II-IV-VI compounds.

11. The composite nanoparticle of claim 9 wherein said inorganic semiconductor shell is of a material selected from the group consisting of Group II-VI compounds, Group II-V compounds, Group III-VI compounds, Group III-V compounds, Group IV-VI compounds, Group I-III-VI compounds, Group II-IV-V compounds, and Group II-IV-VI compounds.

12. The composite nanoparticle of claim 10 wherein said metallic material shell is of a material selected from the group consisting of cobalt, nickel, iron, iron-platinum, iron oxide, and a magnesium iron oxide spinel.

13. The composite nanoparticle of claim 1 wherein said nanoparticle includes a magnetic material core of cobalt and an inorganic semiconductor shell of cadmium selenide.

14. The composite nanoparticle of claim 1 furhter including a spacer material between said core and said shell, said spacer material selected from the group consisting of dielectric materials and inorganic semiconductor materials of a thickness or composition so as to function essentially solely as a spacer material.

15. The composite nanoparticle of claim 11 further including a spacer material between said core and said shell, said spacer material selected from the group consisting of dielectric materials and inorganic semiconductor materials of a thickness or composition so as to function essentially solely as a spacer material.

16. The composite nanoparticle of claim 12 further including a spacer material between said core and said shell, said spacer material selected from the group consisting of dielectric materials and inorganic semiconductor materials of a thickness or composition so as to function essentially solely as a spacer material.

17. The composite nanoparticle of claim 1 further including a passivating layer upon said shell layer.

18. The composite nanoparticle of claim 11 further including a passivating layer upon said shell layer.

19. The composite nanoparticle of claim 16 further including a passivating layer upon said shell layer.

* * * * *